United States Patent
Imaida et al.

(10) Patent No.: US 9,445,931 B2
(45) Date of Patent: Sep. 20, 2016

(54) WALKING ASSIST DEVICE

(75) Inventors: Masayuki Imaida, Ichinomiya (JP); Koji Osawa, Okazaki (JP)

(73) Assignee: TOYOTA JIDOSHA KABUSHIKI KAISHA, Toyota-Shi (JP)

( * ) Notice: Subject to any disclaimer, the term of this patent is extended or adjusted under 35 U.S.C. 154(b) by 895 days.

(21) Appl. No.: 13/616,838

(22) Filed: Sep. 14, 2012

(65) Prior Publication Data
US 2013/0012852 A1 Jan. 10, 2013

Related U.S. Application Data

(63) Continuation of application No. PCT/JP2010/072680, filed on Dec. 16, 2010.

(51) Int. Cl.
*A61F 5/01* (2006.01)
*A61H 1/02* (2006.01)
*A61H 3/00* (2006.01)
*F16F 9/14* (2006.01)

(52) U.S. Cl.
CPC ............. *A61F 5/01* (2013.01); *A61H 1/024* (2013.01); *A61H 3/00* (2013.01); *F16F 9/145* (2013.01); *A61H 2201/0165* (2013.01); *A61H 2201/1671* (2013.01); *A61H 2201/50* (2013.01); *A61H 2201/5064* (2013.01); *A61H 2201/5069* (2013.01)

(58) Field of Classification Search
CPC .. A61H 1/0237; A61H 1/024; A61H 1/0244; A61H 3/00; A61H 2201/1436; A61H 2201/1445
See application file for complete search history.

(56) References Cited

U.S. PATENT DOCUMENTS

| | | | |
|---|---|---|---|
| 7,578,799 B2 * | 8/2009 | Thorsteinsson et al. | 602/5 |
| 2006/0249315 A1 * | 11/2006 | Herr | A61F 2/60 180/8.1 |
| 2007/0056592 A1 | 3/2007 | Angold et al. | |
| 2007/0123997 A1 * | 5/2007 | Herr et al. | 623/27 |
| 2007/0270976 A1 * | 11/2007 | DeHarde et al. | 623/27 |
| 2008/0255489 A1 | 10/2008 | Genda | |
| 2009/0076618 A1 | 3/2009 | Auberger | |
| 2010/0125229 A1 * | 5/2010 | Rudolph et al. | 602/16 |
| 2011/0040216 A1 * | 2/2011 | Herr | A61F 2/60 601/34 |

FOREIGN PATENT DOCUMENTS

| | | |
|---|---|---|
| CN | 101175456 A | 5/2008 |
| EP | 1 792 597 A | 6/2007 |
| JP | 63-43036 A | 2/1988 |
| JP | 2006-061460 A | 3/2006 |
| JP | 2007-252514 A | 10/2007 |
| JP | 2008-253539 A | 10/2008 |
| JP | 2009-629927 A | 8/2009 |
| JP | 2010-148638 A | 7/2010 |
| JP | 4550137 B2 | 9/2010 |
| JP | 2011-193901 A | 10/2011 |

OTHER PUBLICATIONS

International Search Report mailed Mar. 22, 2011 & Written Opinion of PCT/JP2010/072680.

* cited by examiner

*Primary Examiner* — Justine Yu
*Assistant Examiner* — Kathrynn Lyddane
(74) *Attorney, Agent, or Firm* — Kenyon & Kenyon LLP

(57) ABSTRACT

A walking assist device having a safety mechanism that mitigates an impact upon falling is provided. A walking assist device has an upper and lower leg links, a motor, and a controller. The controller controls the motor to apply torque to the lower leg link. The walking assist device also has a one-way damper which generates a resisting force against rotation of the lower leg link in the knee bending direction, and does not generate a resisting force against rotation of the lower leg link in the knee straightening direction. The controller engages the one-way damper while controlling the motor to apply torque to the lower leg link in the knee straightening direction, and disengages the one-way damper while controlling the motor to apply torque to the lower leg link in the knee bending direction.

3 Claims, 4 Drawing Sheets

WALKING ASSIST DEVICE

CROSS-REFERENCE TO RELATED APPLICATION

This is a Continuation of International Application No. PCT/JP2010/072680 filed on Dec. 16, 2010, the disclosure of which is hereby incorporated by reference herein in its entirety.

TECHNICAL FIELD

The present invention relates to a walking assist device which assists a walking motion of a user.

DESCRIPTION OF THE RELATED ART

Researches have been carried out for a walking assist device which assists a walking motion by applying torque to a knee joint of a user. A typical walking assist device is provided with an upper leg link and a lower leg link which are attached to an upper leg and a lower leg of the user, and an actuator which causes the lower leg link to swing (rotate). Japanese Patent Application Publication No. 2006-61460 discloses one example of a walking assist device of this kind. One application of a walking assist device of this kind is a device for rehabilitation of users who have difficulty in moving his or her leg well. Therefore, desirably, the walking assist device includes safety measures for situations where the user may be about to fall over. The walking assist device according to Japanese Patent Application Publication No. 2006-61460 has an abnormality mode for situations where an abnormality is detected. In this abnormality mode, the walking assist device compulsorily carries out an action for correcting an abnormal walking attitude or shuts off the power of the actuator.

SUMMARY OF THE INVENTION

Compulsorily carrying out the action for correcting the attitude includes driving the actuator. If an abnormality has occurred, it is not advisable to drive the actuator. The reason for this is that there is a risk of active movement of the lower leg link causing undesirable effects to the user. On the other hand, if the power of the actuator is simply shut off, then the power of the actuator which has been supporting the body weight suddenly disappears, and there is a risk of causing an impact to the user upon falling. The present specification provides a walking assist device provided with a safety mechanism which mitigates an impact upon falling, without actively driving a lower leg link.

The novel walking assist device disclosed by the present specification comprises: an upper leg link to be attached to an upper leg of a user; a lower leg link to be attached to a lower leg of the user; and an actuator and a controller. The lower leg link is rotatably connected to the upper leg link. The upper leg link and the lower leg link are composed in such a manner that, when the walking assist device is attached to a user, a rotational axis of the lower leg link with respect to the upper leg link substantially coincides with a rotational axis of the knee joint of the user. The actuator is typically a motor, which can apply torque to the lower leg link. The controller controls the actuator so that an angle of rotation of the lower leg link follows a predetermined target pattern of the knee angle. The target pattern represents changes in the knee angle during walking.

This walking assist device also comprises a one-way damper. The one-way damper is configured to generate a resisting force against rotation of the lower leg link in a knee bending direction, but not to generate a resisting force against rotation of the lower leg link in a knee straightening direction. It should be noted that although the description states "not to generate a resisting force", a slight mechanical resistance (such as friction loss), and the like, is allowed. The controller switches the one-way damper to engage and disengage the one-way damper with/from the lower leg link. Stated alternatively, "engaging" means activating. Stated alternatively, "disengaging" means deactivating. When the one-way damper is engaged with the lower leg link, the lower leg link rotates readily in the knee straightening direction but cannot rotate readily in the knee bending direction. When the one-way damper is disengaged from the lower leg link, the lower leg link rotates readily in both directions. The controller engages the one-way damper while controlling the actuator to apply torque to the lower leg link in the knee straightening direction, and disengages the one-way damper while controlling the actuator to apply torque to the lower leg link in the knee bending direction.

DETAILED DESCRIPTION OF INVENTION

Representative, non-limiting examples of the present invention will now be described in further detail with reference to the attached drawings. This detailed description is merely intended to teach a person of skill in the art further details for practicing preferred aspects of the present teachings and is not intended to limit the scope of the invention. Furthermore, each of the additional features and teachings disclosed below may be utilized separately or in conjunction with other features and teachings to provide improved walking assist device, as well as methods for using and manufacturing the same.

Moreover, combinations of features and steps disclosed in the following detailed description may not be necessary to practice the invention in the broadest sense, and are instead taught merely to particularly describe representative examples of the invention. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Embodiments

Figure 1:
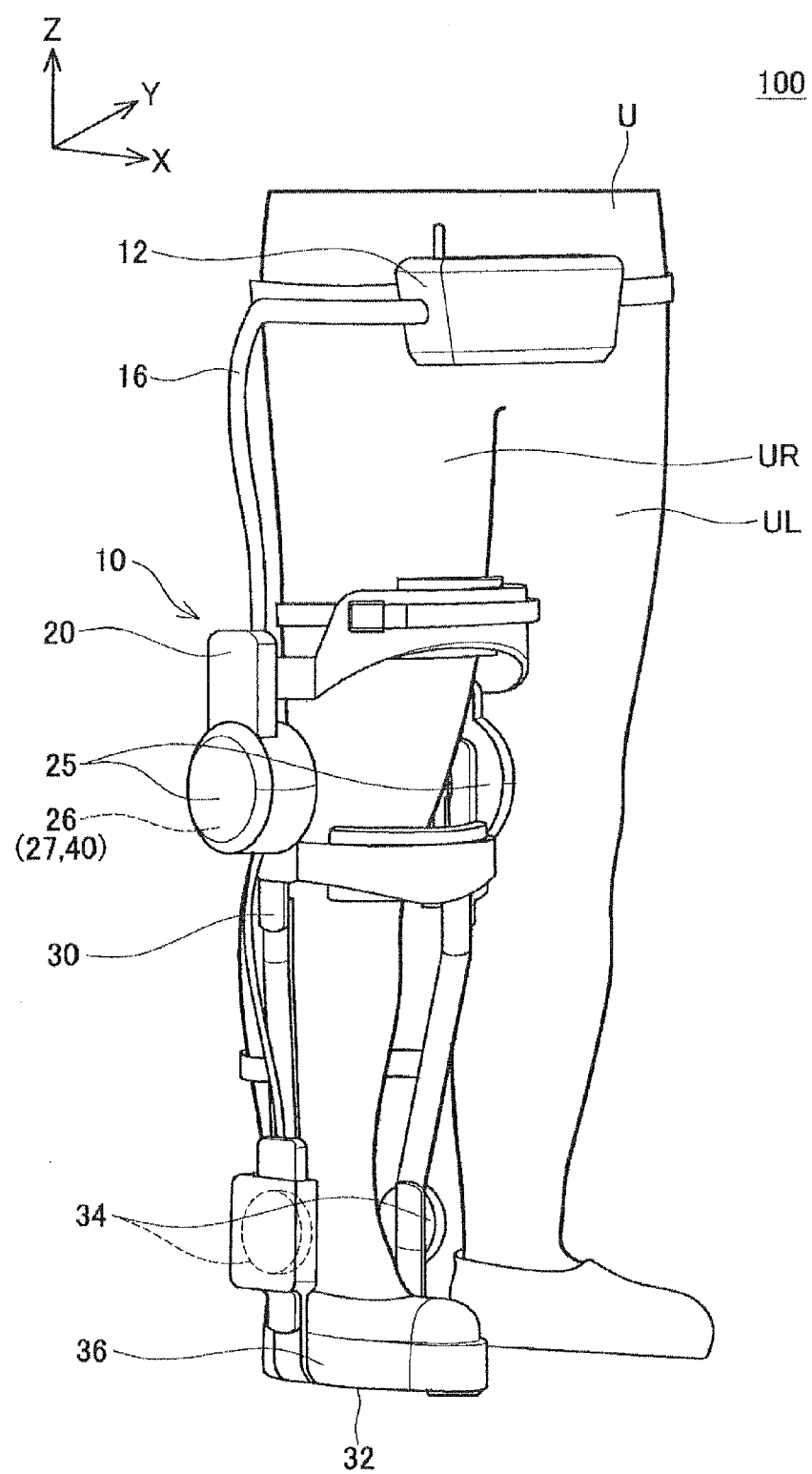
FIG. 1 shows a schematic perspective view of a walking assist device.

FIG. 1 shows a schematic view of a walking assist device 100 according to a first embodiment. The walking assist device 100 is mainly configured of a leg attachment 10 which is attached to a right leg UR of a user U, and a controller 12 which controls the leg attachment 10. In the present embodiment, it is presumed that the user U is patient whose left leg UL is a healthy leg, but who cannot move his or her right leg UR well. Since the left leg UL is a healthy leg, the leg attachment 10 is attached to the right leg UR only. The right leg UR to which the leg attachment is attached may be called the "attached leg" below. Furthermore, the left leg UL may be called a "sound leg".

Before describing the walking assist device 100, the coordinates system will be explained. As shown in FIG. 1, an X axis is set toward the front of the user U, a Y axis is set toward the side of the user, and a Z axis is set vertically upwards. In the technical field of robots, generally, an axis which extends in the front/rear direction of the robot (human) (X axis) is called a roll axis, an axis which extends to the side of the robot (human) (Y axis) is called a pitch axis, and an axis which extends vertically upwards (Z axis) is called a yaw axis.

The structure of the leg attachment 10 will now be described. The leg attachment 10 comprises an upper leg link 20, a lower leg link 30 and a foot link 36. The upper leg link 20 is to be attached to an upper leg of the user, the lower leg link 30 is to be attached to a lower leg of the user, and the foot link 36 is to be attached to a foot of the user.

The upper leg link 20 and the lower leg link 30 are connected on both sides of the right knee joint of the user. More specifically, the upper leg link 20 and the lower leg link 30 are connected to each other rotatably by a pair of first joints 25 which is positioned coaxially with the knee joint of the user. A motor 26, an angle sensor 27 and a one-way damper 40 are incorporated inside the first joint 25 on the outer side. The motor 26 applies torque to the lower leg link 30 and causes the lower leg link 30 to swing (rotate) about a knee pitch axis. Below, the angle formed by the upper leg link 20 and the lower leg link 30 is called a "knee angle". The angle measured by the angle sensor 27 is the swing angle of the lower leg link 30 with respect to the upper leg link 20, and this angle also corresponds to the knee angle formed by the upper leg and the lower leg of the user. The structure of the one-way damper 40 is described in detail below.

The lower leg link 30 and the foot link 36 are connected via second joints 34 which are positioned on both sides of the user's ankle joint. The second joints 34 are not equipped with an actuator, and the foot link 36 swings passively in accordance with the swinging movement of the right foot of the user U. A grounding sensor 32 is disposed on a sole of the foot link 36. The grounding sensor 32 detects whether or not the right leg UR is grounded.

The controller 12 is attached to the waist of the user U by a belt. The controller 12 incorporates a built-in micro computer and a battery, and supplies electricity to the respective parts of the leg attachment 10 via a cable 16, as well as controlling the operation of the respective parts of the leg attachment 10. The controller 12 controls the motor 26 based on the sensor data from the angle sensor 27 and the grounding sensor 32. The motor 26 applies torque to the right knee joint so that the lower leg of the right leg swings appropriately in accordance with a walking motion of the user. For example, when the right leg is detected to have lifted from the ground, the controller 12 controls the motor 26 so that the angle of the lower leg link 30 (the knee angle) follows a predetermined target pattern. Normally, a knee rotates in a bending direction in a first half of a swing phase, and rotates in a straightening direction in a second half of the swing phase. The target pattern is time series data of a target knee angle, in which the target knee angle changes to the knee bending direction in the first half of the swing phase and the target knee angle changes to the knee straightening direction in the second half of the swing phase. The controller 12 controls the motor 26 so that the actual knee angle measured by the angle sensor 27 follows the target pattern.

Figure 2:
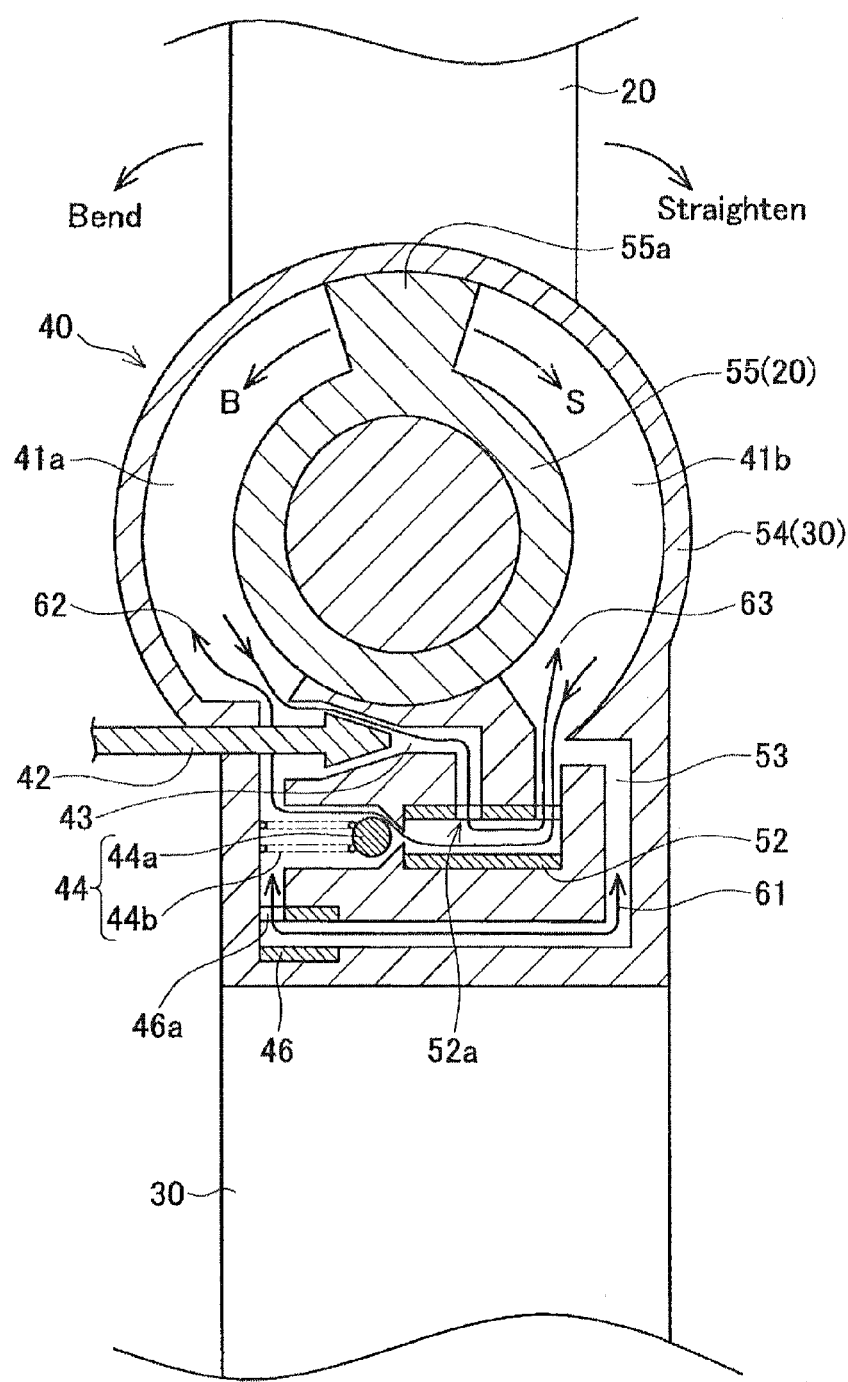
FIG. 2 is a cross-sectional view of a one-way damper.
Figure 3:
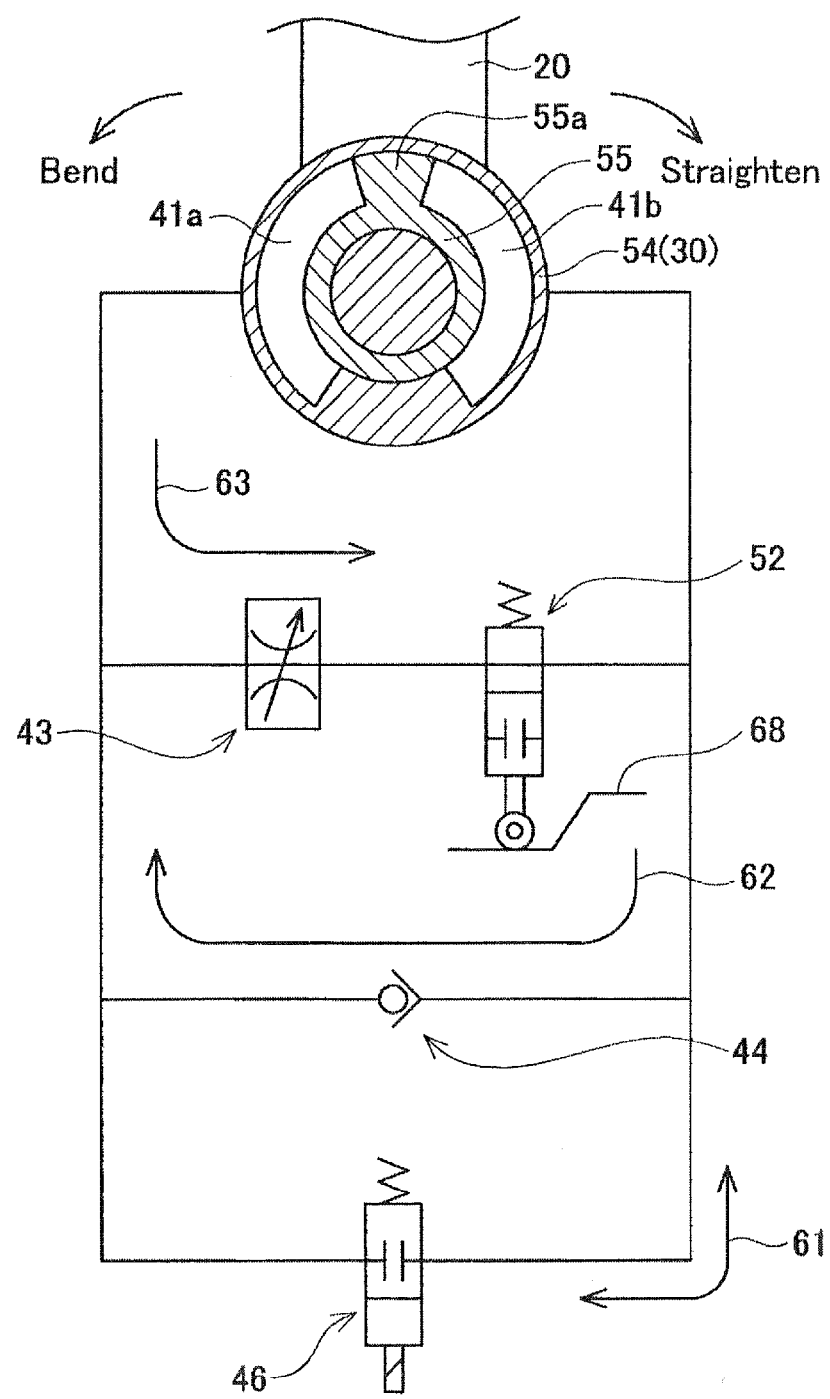
FIG. 3 is a block diagram showing a composition of the one-way damper.

The structure of the one-way damper 40 will now be described. FIG. 2 is a cross-sectional diagram showing a mechanical structure of a one-way damper 40, and FIG. 3 is a block diagram of the one-way damper 40. The case 54 of the one-way damper 40 is fixed to the lower leg link 30 and a rotating shaft 55 of the one-way damper 40 is fixed to the upper leg link 20. In FIG. 2 and FIG. 3, clockwise rotation of the upper leg link 20 (counter-clockwise rotation of the lower leg link 30) corresponds to rotating in the knee straightening direction, and counter-clockwise rotation of the upper leg link 20 (clockwise rotation of the lower leg link 30) corresponds to rotating in the knee bending direction.

An oil space 41 which is filled with oil is provided inside the case 54. The oil space 41 is divided into two spaces, a bending side oil space 41a and a straightening side oil space 41b, by a partition 55a which is provided in projecting fashion on an outer circumference of the rotating shaft 55. As shown in FIG. 2, when the upper leg link 20 (the lower leg link 30) rotates in the knee bending direction, the partition 55a rotates in the counter-clockwise direction, the bending side oil space 41a becomes narrow and the straightening side oil space 41b becomes wide. Conversely, when the upper leg link 20 (the lower leg link 30) rotates in the knee straightening direction, the partition 55a rotates in the clockwise direction, the straightening side oil space 41b becomes narrow and the bending side oil space 41a becomes wide.

The bending side oil space 41a and the straightening side oil space 41b are connected by three flow channels, and the rotation resistance of the one-way damper 40 (in other words, the ease of rotation of the lower leg link 30) is determined by the ease of flow of the oil through the flow channels. The first flow channel 61 passes through a bypass valve 46. The second flow channel 62 passes through a check valve 44. The third flow channel 63 passes through an orifice 43 and an orifice closing valve 52.

The first flow channel 61 simply connects the bending side oil space 41a and the straightening side oil space 41b, and a bypass valve 46 is provided at an intermediate point of the flow channel. When the bypass valve 46 opens, the first flow channel 61 opens, and thus, the bending side oil space 41a and the straightening side oil space 41b are connected. Oil can flow bi-directionally without resistance between the bending side oil space 41a and the straightening side oil space 41b via the first flow channel 61. If the motor 26 is OFF, then the controller 12 opens the bypass valve 46. Consequently, the lower leg link 30 is able to rotate readily in both the knee bending direction and knee straightening direction. When the bypass valve 46 is closed, the oil can no longer pass along the first flow channel 61. The bypass valve 46 is a cylinder which is disposed in the first flow channel 61, and the valve opening 46a is switched between open and closed by rotation of this cylinder.

The second flow channel 62 passes through a check valve 44. The check valve 44 is constituted by a check ball 44a and a spring 44*b* which presses the check ball 44*a*. The spring 44*b* presses the check ball 44*a* from the bending side oil space 41*a* towards the straightening side oil space 41*b*. The check valve 44 allows the oil to pass without resistance at all times from the straightening side oil space 41*b* to the bending side oil space 41*a*. Conversely, the check valve 44 does not allow oil to pass from the bending side oil space 41*a* to the straightening side oil space 41*b*.

The third flow channel 63 passes through the orifice 43 and the orifice closing valve 52. The orifice 43 can narrow the oil flow channel. The narrower the flow channel, the greater the flow channel resistance is produced against the flow of oil. In other words, when the oil passes along the third flow channel 63, the rotation of the lower leg link 30 receives a large resistance. The rotation resistance of the lower leg link 30 (the flow channel resistance of the orifice 43) is adjusted by an orifice adjusting valve 42.

When the orifice closing valve 52 closes, the third flow channel 63 closes. The orifice closing valve 52 is a cylinder which is disposed in the second flow channel 62, and a valve opening 52*a* is switched between open and closed by rotation of this cylinder. The orifice closing valve 52 opens and closes in coordination with the angle of rotation (knee angle) of the lower leg link 30. The reference numeral 68 in FIG. 3 schematically represents a cam lever 68 which is fixed to the upper leg link 20. Although the specific structure is not depicted in the drawings, the cam lever 68 fixed to the upper leg link 20 contacts the opening/closing lever of the orifice closing valve 52 which is fixed to the lower leg link 30. The cam lever 68 opens or closes the orifice closing valve 52 in accordance with the relative rotation of the upper leg link 20 and the lower leg link 30. The operation of the cam lever 68 is described with reference to FIG. 3 as follows. The cam lever 68 moves leftwards or rightwards in FIG. 3, in accordance with the relative rotation of the upper leg link 20 and the lower leg link 30. When the cam lever 68 moves leftwards, so the orifice closing valve 52 is pushed up and the valve closes. As described below, the orifice closing valve 52 can also be controlled from the controller 12.

The bypass valve 46, the orifice closing valve 52 and the orifice adjusting valve 42 are controlled by the controller 12. When the controller 12 closes the bypass valve 46 and opens the orifice closing valve 52, then the oil flows smoothly from the straightening side oil space 41*b* to the bending side oil space 41*a* along the second flow channel (check valve 44). On the other hand, oil is not able to flow from the bending side oil space 41*a* to the straightening side oil space 41*b* via the second flow channel (check valve 44). Instead, the oil is able to flow slowly from the bending side oil space 41*a* to the straightening side oil space 41*b* via the third flow channel 63 (orifice 43). In other words, when the controller 12 closes the bypass valve 46 and opens the orifice closing valve 52, then the lower leg link 30 is able to rotate freely in the knee straightening direction, but receives resistance against rotation in the knee bending direction (in a case where the motor 26 is not drove). Closing the bypass valve 46 and opening the orifice closing valve 52 operated by the controller 12 correspond to "engaging the one-way damper". In other words, when the controller 12 engages the one-way damper 40, the one-way damper 40 generates a resisting force against rotation of the lower leg link 30 in the knee bending direction and does not generate a resisting force against rotation of the lower leg link 30 in the knee straightening direction. The rotation resisting force can be adjusted by the orifice adjusting valve 42. The orifice adjusting valve 42 is also controlled by the controller 12.

When the controller 12 opens the bypass valve 46, the oil flows smoothly in both directions. Consequently, the lower leg link 30 is able to rotate in both the knee straightening direction and the knee bending direction, without resistance. Opening the bypass valve 46 corresponds to "disengaging the one-way damper".

When the controller 12 closes the orifice closing valve 52 and also closes the bypass valve 46, then the oil is able to flow from the bending side oil space 41*a* to the straightening side oil space 41*b* through the second flow channel 62, but is not able to flow in the reverse direction. In other words, in this case, the lower leg link 30 is permitted to rotate in the knee straightening direction and is prohibited from rotating in the knee bending direction. Stated alternatively, the one-way damper 40 has a function of a one-way clutch which permits rotation of the lower leg link 30 in the knee straightening direction, but prohibits rotation of the lower leg link 30 in the knee bending direction. The one-way damper 40 having the structure shown in FIG. 2 can withstand a load of 50 Nm when prohibiting rotation in the knee bending direction, in one example. Furthermore, one example of the pressure of the oil sealed inside the bending side oil space 41*a* and the straightening side oil space 41*b* is 1.5 MPa.

The controller 12 controls the one-way damper 40 simultaneously with controlling the motor 26. Here, "control the one-way damper" means switching the engaging and disengaging of the one-way damper at a prescribed timing. More specifically, the controller 12 engages the one-way damper 40 when controlling the motor 26 to apply torque to the lower leg link 30 in the knee straightening direction. Furthermore, the controller 12 disengages the one-way damper 40 when controlling the motor 26 to apply torque to the lower leg link 30 in the knee bending direction. If supply of electricity to the motor 26 is shut off for some reason while the one-way damper 40 is engaged, then the leg attachment 10 cannot support the body weight and the lower leg link 30 may go to rotate in the knee bending direction. In this case, the one-way damper 40 is activated and the lower leg link 30 rotates slowly in the knee bending direction. In other words, the user's body is lowered slowly. Consequently, an impact in the event of falling is mitigated.

On the other hand, the one-way damper 40 is disengaged while the motor 26 applies torque in the knee bending direction. The motor 26 does not receive resistance from the one-way damper 40.

As stated previously, the one-way damper 40 can permit rotation of the lower leg link 30 in the knee straightening direction and prohibit rotation in the knee bending direction only. The controller 12 controls the one-way damper 40 appropriately, in accordance with each phase during walking. Next, a detailed control sequence of the one-way damper corresponding to each timing in a walking motion by the controller 12 will be described. Before this description, the definition of the knee angle in the present embodiment will be described. In the present embodiment, when the knee is fully stretched, in other words, when the upper leg and the lower leg are aligned in substantially a single straight line, then the knee angle is defined as zero, and the knee bending direction is defined as a positive direction of the knee angle. For example, when the upper leg and the lower leg are perpendicular, then the knee angle is 90°.

The sequence of controlling the one-way damper 40 performed by the controller 12 is now described. When the attached leg grounds, in other words, when the knee angle has reached zero, the controller 12 closes the bypass valve 46 and also closes the orifice closing valve 52. In so doing, the lower leg link 30 is permitted to rotate in the knee straightening direction and is prohibited from rotating in the knee bending direction. The controller 12 permits rotation of the lower leg link 30 in the knee straightening direction and prohibits rotation thereof in the knee bending direction, while the attached leg is in the stance phase. When the attached leg grounds, the controller 12 opens the bypass valve 46. In other words, the controller 12 makes the lower leg link 30 freely rotatable in both the knee straightening direction and the knee bending direction. However, since the controller 12 applies torque in the knee bending direction to the lower leg link 30, then the lower leg link 30 does not actually rotate in the knee straightening direction. In this case, the controller 12 opens the orifice closing valve 52.

When the attached leg grounds, the controller 12 closes the bypass valve 46 and opens the orifice closing valve 52. In other words, the controller 12 engages the one-way damper 40. In this case, the lower leg link 30 is able to rotate freely in the knee straightening direction, but receives resistance to rotation in the knee bending direction.

Next, the control of the one-way damper 40 by the controller 12 when an abnormality of some kind has occurred will be described. Upon detecting an abnormality of some kind, the controller 12 shuts off supply of electricity to the motor 26, and also closes the bypass valve 46 and opens the orifice closing valve 52. In other words, the controller 12 shuts off the supply of electricity to the motor 26 and also engages the one-way damper 40, when the abnormality is detected. According to operations hereof, the lower leg link 30 rotates slowly in the knee bending direction, due to the user's body weight. In other words, the walking assist device 100 functions to slowly lower the hip position of the user.

Next, a walking assist device according to a second embodiment will be described. Stated alternatively, the walking assist device 100 according to the first embodiment is able to switch between a mode which permits free rotation of the lower leg link 30, a mode which applies resistance to rotation of the lower leg link 30 in one direction (the knee bending direction) only (and freely permits rotation in the opposite direction), and a mode which prohibits rotation of the lower leg link 30 in one direction (the knee bending direction) only (and freely permits rotation in the opposite direction). Below, a mode which permits free rotation of the lower leg link 30 in both directions is called a free mode, a mode which applies resistance to rotation of the lower leg link 30 in one direction only is called a damper mode, and a mode which prohibits rotation of the lower leg link 30 in one direction only is called a lock mode. The walking assist device according to the second embodiment comprises a further one-way damper according to the first embodiment. The one-way damper according to the first embodiment is called a first damper and the added one-way damper is called a second damper hereinafter. The second damper restricts rotation in the opposite direction to the first damper. The first damper and the second damper are controlled respectively and independently. More specifically, the walking assist device of the second embodiment can switch between (can be set to) the free mode, the damper mode and the lock mode in respect to the rotation of the lower leg link 30 in the knee bending direction, and can switch between (can be set to) the free mode, the damper mode and a the lock mode in respect to the rotation of the lower leg link 30 in the knee bending direction.

Figure 4:
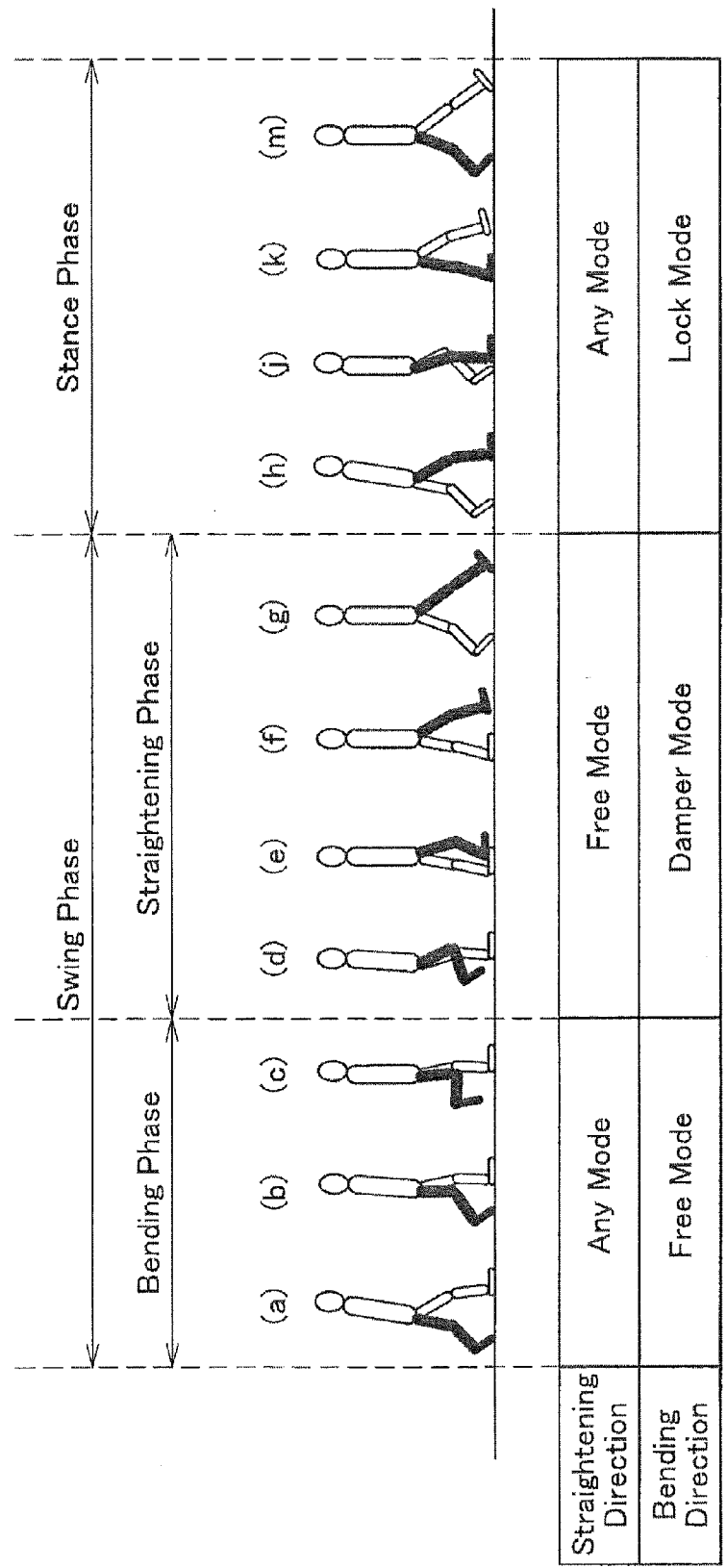
FIG. 4 is a diagram illustrating a control sequence of a walking assist device according to a second embodiment.

FIG. 4 shows a relationship between respective timings in a walking motion and a control sequence of the first and second one-way dampers. The leg colored black in the simplified human drawing indicates the attached leg. (a) to (g) in the simplified human drawing indicate the configuration of the leg when the attached leg is in a swing phase, and (h) to (m) indicate the configuration of the leg when the attached leg in a stance phase. The swing phase is further divided into a bending phase ((a) to (c)) in which the lower leg swings in the knee bending direction, and a straightening phase ((d) to (g)) in which the lower leg swings in the knee straightening direction.

The line stating "Straightening Direction" on the lower side in FIG. 4 indicates a control mode of the second one-way damper, and the line stating "Bending Direction" indicates a control mode of the first one-way damper. In the bending phase of the swing phase, the walking assist device sets the first one-way damper to the free mode. The second one-way damper may be in any mode. In the straightening phase of the swing phase, the walking assist device sets the first one-way damper to the damper mode and sets the second one-way damper to the free mode. In the stance phase, the walking assist device sets the first one-way damper to the lock mode. The second one-way damper may be in any mode. In the bending phase of the swing phase, the walking assist device applies torque to the lower leg link in the knee bending direction, and in the straightening phase thereof, the walking assist device applies torque to the lower leg link in the knee straightening direction.

A modification example of the control sequence explained above will now be described. The walking assist device controls the one-way damper and increases the resistance in the bending direction, when grounding of the attached leg is detected in the bending phase of the swing phase. Grounding does not normally occur in the bending phase of the swing phase, and therefore grounding during the bending phase has a high probability of being due to an unforeseen situation. In a situation of this kind, it is possible to mitigate the impact upon falling, by increasing the resistance in the bending direction. This modification can be expressed in the following terms. The walking assist device comprises the one-way damper which generates the resisting force against rotation of the lower leg link in the knee bending direction, and does not generate the resisting force against rotation of the lower leg link in the knee straightening direction. The controller engages the one-way damper while controlling the actuator to apply torque to the lower leg link in the knee straightening direction, and disengages the one-way damper while controlling the actuator to apply torque to the lower leg link in the knee bending direction. Moreover, if the grounding of the leg is detected while the leg to which the lower leg link is attached is in the swing phase and the lower leg is swinging in the knee bending direction, then the controller sets the rotation resisting force of the one-way damper to a larger value than the rotation resisting force "while controlling the actuator to apply torque to the lower leg link in the knee straightening direction".

In the walking assist device, preferably, the second one-way damper (the damper which restricts rotation of the lower leg link in the knee straightening direction) in the straightening phase of the swing phase of the attached leg may be set to the damper mode instead of the free mode, in the control sequence in FIG. 4.

In the walking assist device, preferably, the first one-way damper (the damper which restricts rotation of the lower leg link in the knee bending direction) may be switched to the lock mode, when an abnormality of some kind is detected during the straightening phase of the swing phase of the attached leg.

Some points of concern regarding the above described embodiments will be noted below. In a normal walking action, a lower leg of a user rotates in a knee bending direction in a first half of a swing phase and rotates in a knee straightening direction in a second half of the swing phase. In a walking assist device disclosed herein, a controller controls an actuator to apply torque to a lower leg link in the knee bending direction in the first half of the swing phase and to apply torque to the lower leg link in the knee straightening direction in the second half of the swing phase, in order to achieve the normal walking action. In this walking assist device, if an abnormality of some kind has occurred while the lower leg is rotating in the knee straightening direction during the swing phase and the power of the actuator has declined (or been shut off), the lower leg link is rotated slowly in the knee bending direction due to a one-way damper when the leg grounds. For this reason, the user's body is lowered slowly and an impact upon falling is mitigated.

The walking assist device described herein may continue engagement of the one-way damper while applying torque to the lower leg link in the knee straightening direction. In other words, the walking assist device described above may exhibit an advantage in that a damper is operated immediately when the power of the actuator declines (or is shut off), the leg grounds, and the lower leg link starts to rotate slowly in the knee bending direction due to the body weight.

Preferably, the controller of the walking assist device described herein may shut off supply of electricity to the actuator and engage the one-way damper when an abnormality of some kind is detected, even in cases where the one-way damper is disengaged. In the walking assist device of this kind, when an abnormality is detected, the lower leg link rotates slowly in the knee bending direction due to the body weight and the one-way damper, and the impact upon falling may be mitigated.

Furthermore, preferably, the walking assist device described above may comprise a lock mechanism configured to prohibit rotation of the lower leg link. In a normal state (a state where no abnormality has detected), the controller is configured to engage the lock mechanism while the leg to which the lower leg link is attached is in a stance phase and to disengage the lock mechanism while the leg to which the lower leg link is attached is in the swing phase. In other words, the controller is configured to engage the lock mechanism while the leg to which the lower leg link is attached is grounded, and to disengage the lock mechanism while the leg to which the lower leg link is attached is a swinging leg. During the stance phase where the body weight must be supported firmly, by locking the lower leg link it is possible to support the body weight without power from the actuator, and therefore energy savings can be achieved. On the other hand, the controller disengages the lock mechanism during the swing phase of the leg to which the lower leg link is attached, as well causing the lower leg link to swing (rotate) in accordance with the walking motion, by the actuator.

What is claimed is:

1. A walking assist device comprising:
   an upper leg link to be attached to an upper leg of a user;
   a lower leg link to be attached to a lower leg of the user, the lower leg link being rotatably connected to the upper leg link;
   an actuator configured to apply motor torque to the lower leg link;
   a one-way damper configured to generate a resisting force against rotation of the lower leg link in a knee bending direction and not to generate a resisting force against the rotation of the lower leg link in a knee straightening direction; and
   a controller configured to control the actuator and switch between engaging and disengaging of the one-way damper with/from the lower leg link,
   wherein the controller is configured to:
   control the actuator to apply the motor torque to the lower leg link so that an angle of rotation of the lower leg link follows a predetermined target pattern of the knee angle, the target pattern representing changes in the knee angle during a walking action; and
   engage the one-way damper while controlling the actuator to apply the motor torque to the lower leg link in the knee straightening direction in the swing phase and disengages the one-way damper while controlling the actuator to apply the motor torque to the lower leg link in the knee bending direction in the swing phase.

2. The walking assist device of claim 1, wherein the controller shuts off supply of electricity to the actuator and engages the one-way damper when an abnormality is detected by the controller.

3. The walking assist device of claim 1, further comprising a lock mechanism configured to prohibit the rotation of the lower leg link,
   wherein the controller is configured to engage the lock mechanism when a user's leg is positioned in a stance phase.

* * * * *